(12) United States Patent
Biedermann et al.

(10) Patent No.: US 10,751,101 B2
(45) Date of Patent: *Aug. 25, 2020

(54) DYNAMIC BONE ANCHOR AND METHOD OF MANUFACTURING THE SAME

(71) Applicant: BIEDERMANN TECHNOLOGIES GMBH & CO. KG, Donaueschingen (DE)

(72) Inventors: Lutz Biedermann, VS-Villingen (DE); Wilfried Matthis, Weisweil (DE)

(73) Assignee: BIEDERMANN TECHNOLOGIES GMBH & CO. KG, Donaueschingen (DE)

(*) Notice: Subject to any disclaimer, the term of this patent is extended or adjusted under 35 U.S.C. 154(b) by 109 days.

This patent is subject to a terminal disclaimer.

(21) Appl. No.: 16/148,723

(22) Filed: Oct. 1, 2018

(65) Prior Publication Data

US 2019/0090924 A1    Mar. 28, 2019

Related U.S. Application Data

(63) Continuation of application No. 15/831,124, filed on Dec. 4, 2017, now Pat. No. 10,117,695, which is a (Continued)

(30) Foreign Application Priority Data

Dec. 5, 2012  (EP) .................................... 12195758

(51) Int. Cl.
*A61B 17/86* (2006.01)
*A61B 17/70* (2006.01)
*A61B 17/00* (2006.01)

(52) U.S. Cl.
CPC ........ *A61B 17/8685* (2013.01); *A61B 17/866* (2013.01); *A61B 17/8625* (2013.01);
(Continued)

(58) Field of Classification Search
CPC ....... A61B 17/84; A61B 17/844; A61B 17/86; A61B 17/8625; A61B 17/866; A61B 17/8685

See application file for complete search history.

(56) References Cited

U.S. PATENT DOCUMENTS 5,584,695 A * 12/1996 Lal Sachdeva .... A61B 17/0401
433/173
7,879,036 B2  2/2011 Biedermann et al.
(Continued)

FOREIGN PATENT DOCUMENTS

CN    2453859 Y    10/2001
EP    1 472 983 A1    11/2004
(Continued)

OTHER PUBLICATIONS

Chinese OA for Application No. 201310632148.2, dated Jan. 3, 2017, and English translation (21 pages).
(Continued)

*Primary Examiner* — Christopher J Beccia
(74) *Attorney, Agent, or Firm* — Lewis Roca Rothgerber Christie LLP

(57) ABSTRACT

A dynamic bone anchor includes an anchor member having first and second ends and a tubular section between the ends, a longitudinal axis extending from the first to second end, an outer surface, and a bone engagement structure for engaging a bone on at least a portion of the outer surface; and a longitudinal core member having a first portion and a second portion configured to be received in the tubular section and to connected to the anchor member, with the first portion configured to be spaced apart from the anchor member and movable with respect to it. The core member is made at least partially of a nickel-titanium (Ni—Ti) based shape memory alloy such that its shape after transitioning from a martensitic to austenitic phase is configured to result in a press-fit
(Continued)

connection between the second portion and the anchor member with the second portion in the austenitic phase.

19 Claims, 7 Drawing Sheets

Related U.S. Application Data continuation of application No. 14/098,434, filed on Dec. 5, 2013, now Pat. No. 9,861,415.

(60) Provisional application No. 61/733,769, filed on Dec. 5, 2012.

(52) U.S. Cl.
CPC . *A61B 17/7035* (2013.01); *A61B 2017/00862* (2013.01); *Y10T 29/49826* (2015.01)

(56) References Cited

U.S. PATENT DOCUMENTS

| | | | |
|---|---|---|---|
| 9,861,415 B2 * | 1/2018 | Biedermann | A61B 17/866 |
| 10,117,695 B2 * | 11/2018 | Biedermann | A61B 17/8685 |
| 2004/0220575 A1 | 11/2004 | Biedermann et al. | |
| 2005/0154390 A1 | 7/2005 | Biedermann et al. | |
| 2006/0264954 A1 * | 11/2006 | Sweeney, II | A61B 17/8685 |
| | | | 606/312 |
| 2008/0294204 A1 | 11/2008 | Chirico | |
| 2009/0157123 A1 | 6/2009 | Appenzeller et al. | |
| 2009/0163953 A1 | 6/2009 | Biedermann et al. | |
| 2010/0261034 A1 | 10/2010 | Cardarelli | |
| 2011/0172718 A1 | 7/2011 | Felix et al. | |
| 2011/0276094 A1 | 11/2011 | Kast | |
| 2012/0203286 A1 | 8/2012 | Armstrong et al. | |
| 2013/0245697 A1 | 9/2013 | Hulliger | |
| 2014/0172026 A1 | 6/2014 | Biedermann et al. | |

FOREIGN PATENT DOCUMENTS

| | | |
|---|---|---|
| JP | 2008-535584 A | 9/2008 |
| JP | 2009-90117 A | 4/2009 |
| JP | 2011-506043 A | 3/2011 |
| JP | 2014-521380 A | 8/2014 |
| WO | WO 2007/101267 A1 | 9/2007 |
| WO | WO 2012/158351 A1 | 11/2012 |

OTHER PUBLICATIONS

Extended European Search Report for European Application No. 12195758.3, European Search Report dated Apr. 23, 2013 and dated May 7, 2013 (8 pages).

* cited by examiner

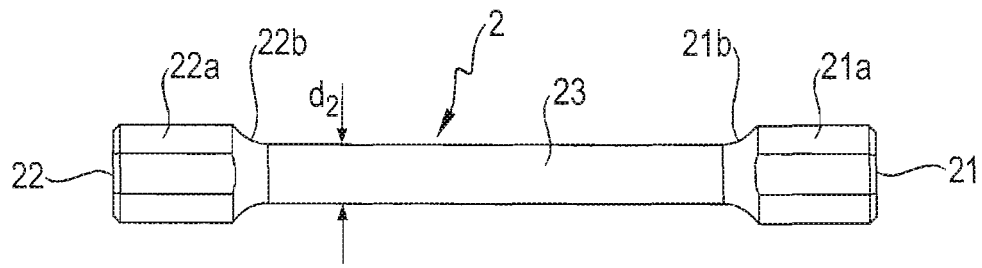
Fig. 4
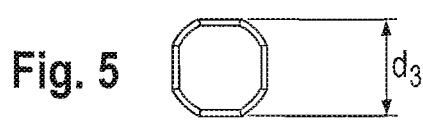
Fig. 5
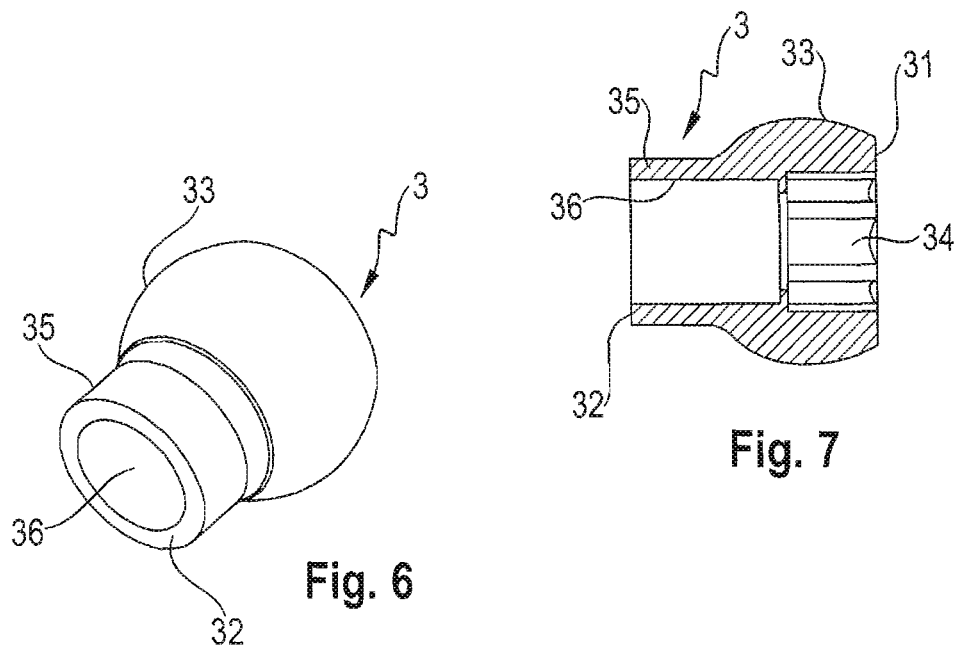
Fig. 6
Fig. 7

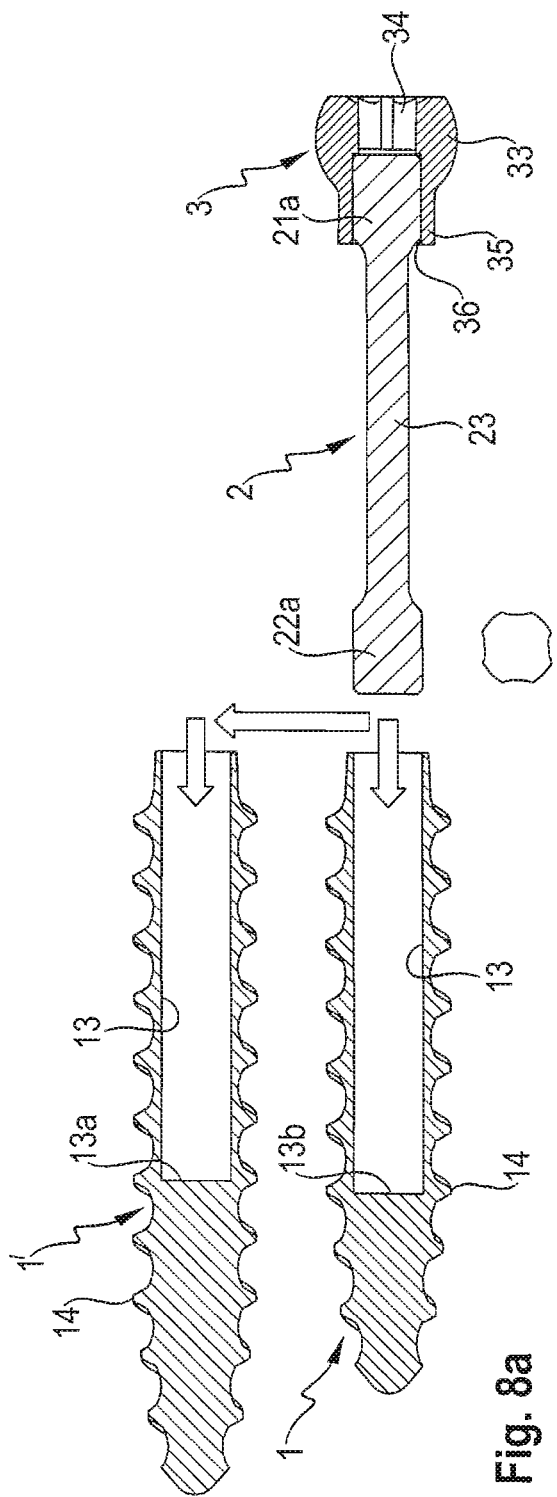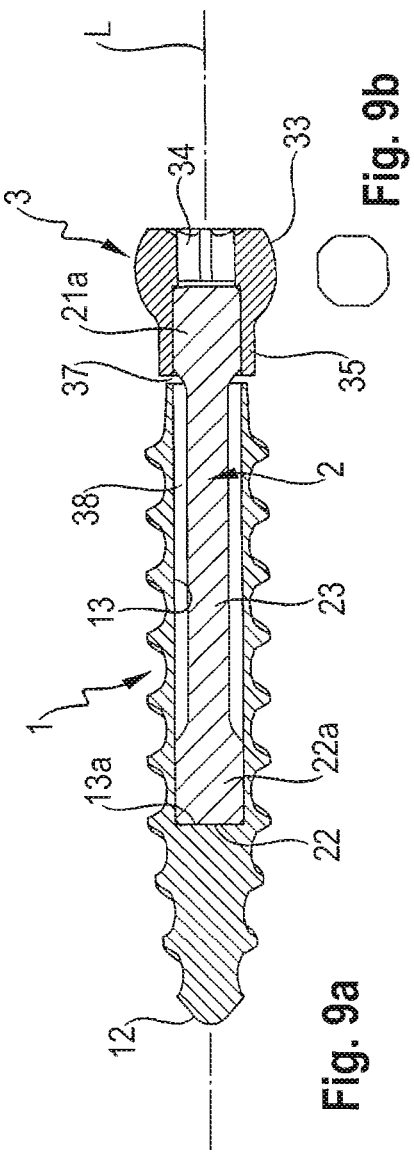

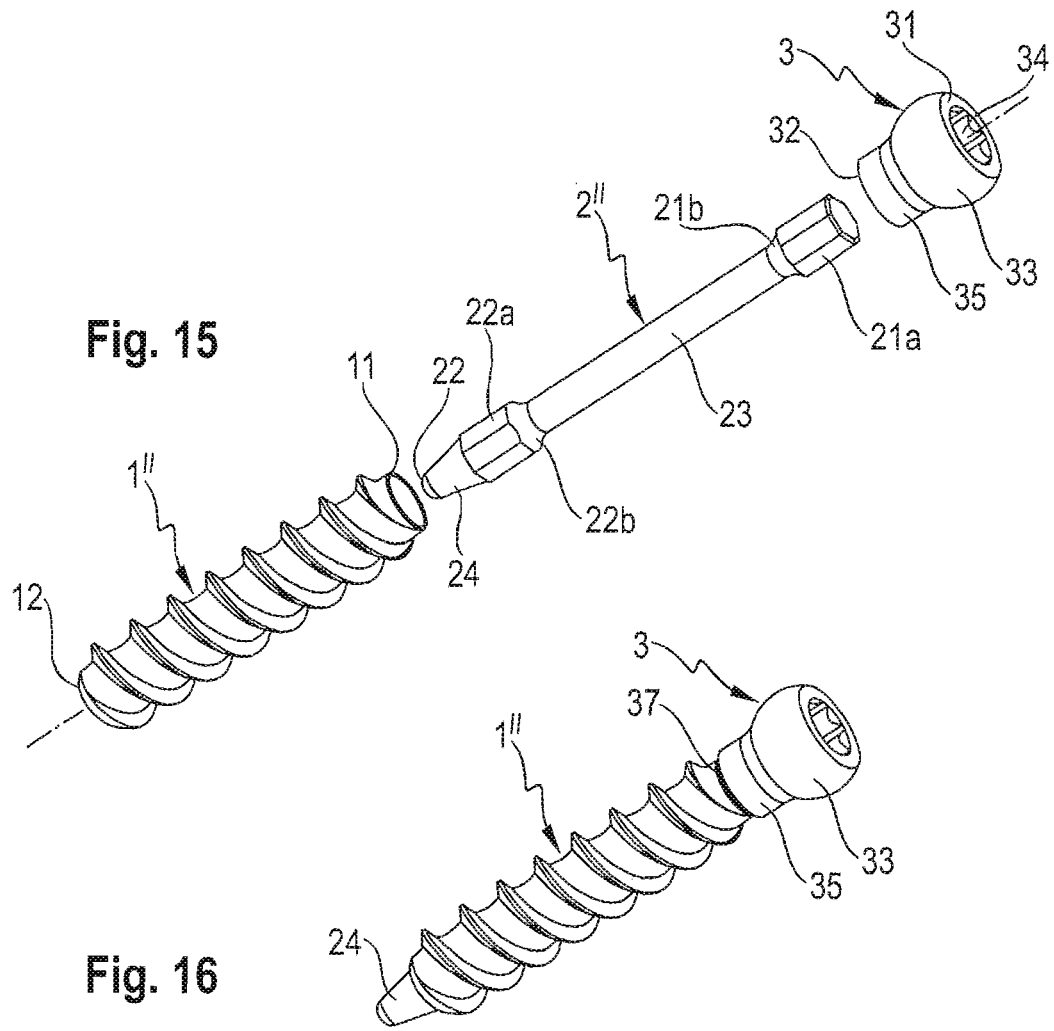
Fig. 15
Fig. 16
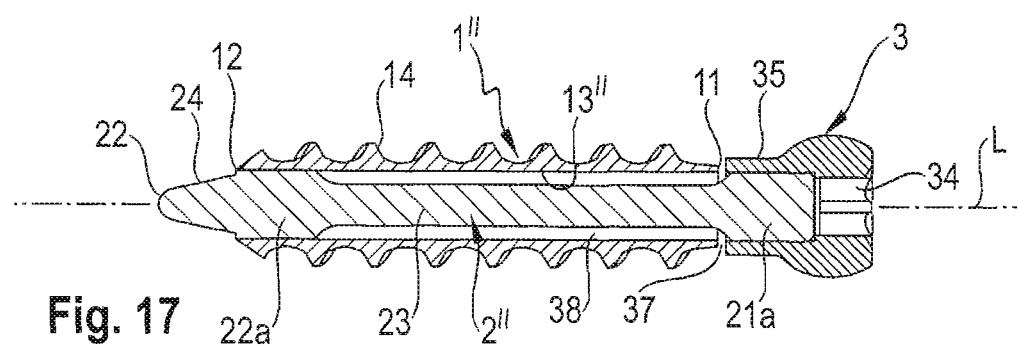
Fig. 17

DYNAMIC BONE ANCHOR AND METHOD OF MANUFACTURING THE SAME

CROSS-REFERENCE TO RELATED APPLICATION(S)

This application is a continuation of U.S. patent application Ser. No. 15/831,124, filed Dec. 4, 2017, which is a continuation of U.S. patent application Ser. No. 14/098,434, filed Dec. 5, 2013, now U.S. Pat. No. 9,861,415, which claims priority to and the benefit of U.S. Provisional Application No. 61/733,769, filed Dec. 5, 2012, in the U.S. Patent and Trademark Office, the entire content of which is incorporated herein by reference; and claims priority from European Patent Application EP 12 195 758.3, filed Dec. 5, 2012, the entire content of which is incorporated herein by reference.

BACKGROUND

1. Field

The invention relates to a dynamic bone anchor and a method of manufacturing a dynamic bone anchor. The dynamic bone anchor comprises an anchor member for anchoring to a bone or a vertebra, and a longitudinal core member provided in the anchor member, a portion of which is movable with respect to the anchor member. The core member is made, at least partially, of a material comprising a nickel-titanium (Ni—Ti) based shape memory alloy having superelastic properties. The method of manufacturing such a dynamic bone anchor makes use of the shape memory effect of the material of the core member. The dynamic bone anchor is particularly applicable in the field of dynamic bone fixation or dynamic stabilization of the spinal column.

2. Description of the Related Art

A dynamic bone anchor is known, for example, from US 2005/0154390 A1. The shaft of the bone anchor comprises an elastic or flexible section.

A further dynamic bone fixation element is known from US 2009/0157123 A1. The dynamic bone fixation element includes a bone engaging component and a load carrier engaging component. The bone engaging component includes a plurality of threads for engaging a patient's bone and a lumen. The load carrier engaging component includes a head portion for engaging a load carrier and a shaft portion that at least partially extends into the lumen. The distal end of the shaft portion is coupled to the lumen and at least a portion of an outer surface of the shaft portion is spaced away from at least a portion of an inner surface of the lumen via a gap so that the head portion can move with respect to the bone engaging component. The load carrier engaging component may be made from a high strength material, for example, a strong metal or metal alloy such as CoCrMo, CoCrMoC, CoCrNi or CoCrWNi. In a particularly preferred embodiment, the bone engaging component is made from titanium or a titanium alloy, while the load carrier engaging portion is made from cobalt chrome (CoCr).

SUMMARY

It is the object of the invention to provide an improved dynamic bone anchor that allows a head of the bone anchor to perform limited motion after anchoring the bone anchor into a bone or a vertebrae. Further, a method of manufacturing such a dynamic bone anchor shall be provided.

With the dynamic bone anchor, bone parts or vertebrae to be fixed or stabilized are able to carry out a controlled limited motion relative to each other. A longitudinal core member provided in the anchor member of the dynamic bone anchor is preferably made of Ni—Ti based shape memory alloy that is in the superelastic metallurgical state under the conditions in which the bone anchor is used in a patient.

Superelasticity, sometimes called pseudoelasticity, involves the creation of stress-induced martensite which simultaneously undergoes strain when it is formed to release the applied stress. When the applied stress is released, the thermally unstable martensite reverts to austenite, and the strain returns to zero. This process results in high elasticity in the material.

Due to the superelastic behavior of the core member, the degree of possible movement of the core member relative to the anchor member is increased compared to materials without superelasticity. The plateau in the stress-strain diagram of a Ni—Ti based shaped memory alloy shows a substantially constant stress exhibited when stress-induced martensite starts forming. This provides for an overload protection, for example during the screwing in of the dynamic bone anchor. In addition, the entire dynamic bone anchor can be designed with a relatively short length, compared to similar bone anchors made of other materials.

The head of the bone anchor can perform rotational and/or translational motions with respect to a central axis of the bone anchor.

The dynamic bone anchor can be provided as a modular system, wherein a core member can be selectively combined with anchor members of different shapes, lengths, or other properties, for example different thread types, barbs etc. This has the advantage that the characteristics of the core member that substantially define the dynamic characteristics of the whole entire dynamic bone anchor, can be utilized in different combinations of core members with anchor members.

By providing core members having different properties, such as their contour, length, etc., and combining them with suitable anchor members, various dynamic properties can be achieved.

With the method of manufacturing the bone anchor that makes use of the shape memory effect of the Ni—Ti shape memory alloy of the core member, the core member can be easily connected to anchor members of different length or other different properties. A resulting press-fit connection between the core member and the anchor member has a higher strength than conventionally generated press-fit connections.

BRIEF DESCRIPTION OF THE DRAWINGS

Further features and advantages of the invention will become apparent from the description of embodiments by means of the accompanying drawings. In the drawings:

FIG. 4: shows a side view of the core member of the dynamic bone anchor according to the first embodiment.

FIG. 5: shows a top view of the core member shown in FIG. 4.

FIG. 6: shows a perspective view of a head of the dynamic bone anchor according to the first embodiment.

FIG. 7: shows a cross-sectional view of the head shown in FIG. 6, the cross-section taken in a plane containing the anchor axis when the head is in a non-deflected state.

FIG. 8a: shows a cross-sectional view of a step of manufacturing the dynamic bone anchor according to the first embodiment, wherein the core member is selectively combined with different anchor members.

FIG. 8b: shows a schematic view of the contour of an end portion of the core member before it is fixed to the anchor member.

FIG. 9a: shows a cross-sectional view of the assembled dynamic bone anchor according to the first embodiment, the cross-section taken in a plane containing the anchor axis.

FIG. 9b: shows a schematic view of the end portion of the core member after inserting the core member into the anchor member, and heating the core member.

FIG. 15: shows a perspective exploded view of a dynamic bone anchor according to a second embodiment.

FIG. 16: shows a perspective view of the dynamic bone anchor according to FIG. 15.

FIG. 17: shows a cross-sectional view of the dynamic bone anchor according to FIG. 16, the cross-section taken in a plane containing the anchor axis.

DETAILED DESCRIPTION

Figure 1:
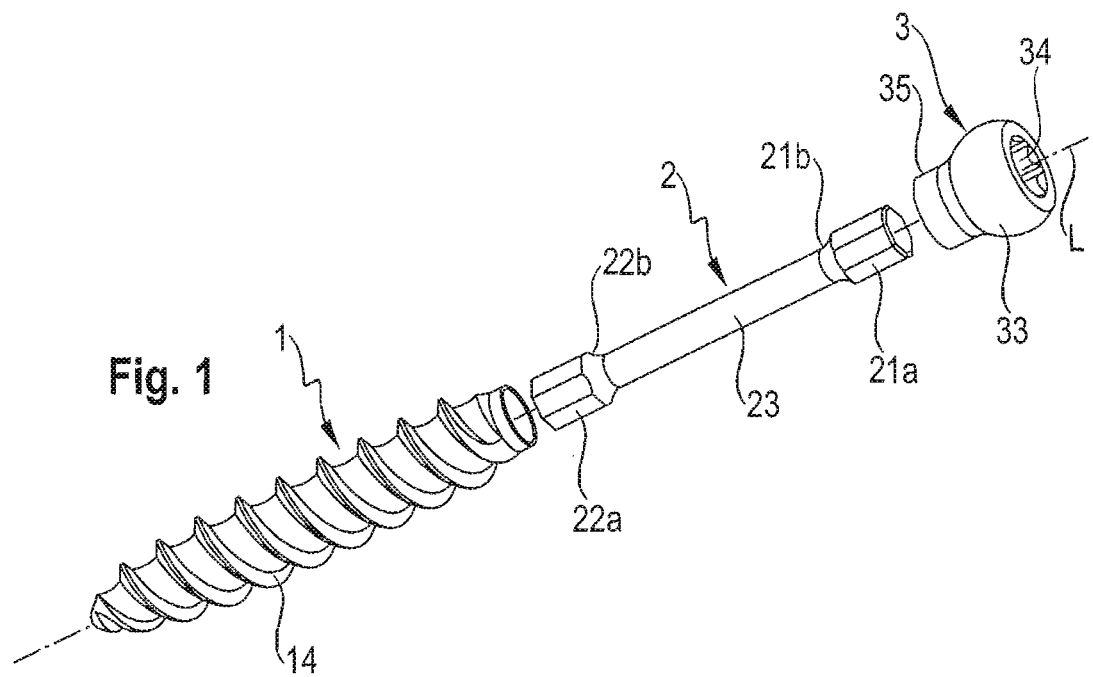
FIG. 1: shows a perspective exploded view of a dynamic bone anchor according to a first embodiment.
Figure 2:
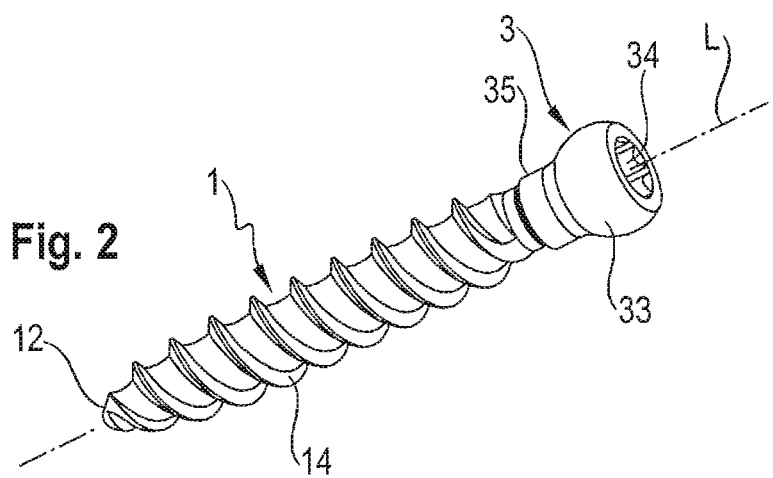
FIG. 2: shows a perspective view of the dynamic bone anchor of FIG. 1 in an assembled state.

As shown in FIGS. 1 and 2, a dynamic bone anchor according to a first embodiment, comprises an anchor member 1 in the form of a screw member, a core member 2 and a head 3. The core member 2 can be inserted into the anchor member 1 and connected thereto, and the head 3 can be connected to the core member 2.

Figure 3:
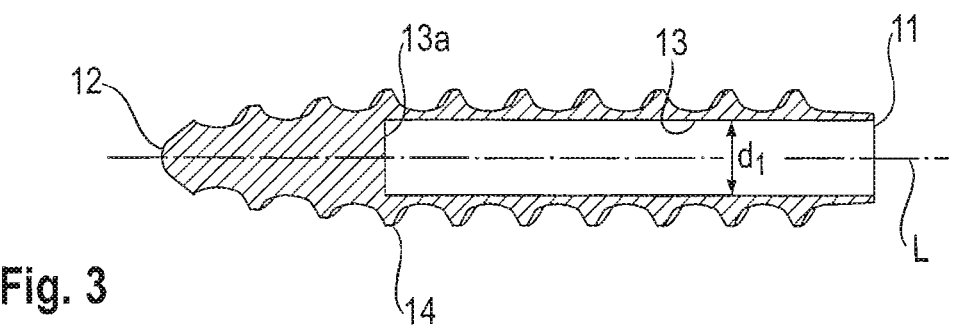
FIG. 3: shows a cross-sectional view of the anchor member of the dynamic bone anchor according to the first embodiment, the cross-section taken in a plane containing the anchor axis.

As further shown in FIG. 3, the anchor member 1 comprises a first end 11, an opposite second end 12, and a longitudinal axis L extending through the first end 11 and the second end 12. The longitudinal axis L forms the central axis of the bone anchor. Adjacent to the first end 11, the anchor member 1 comprises a tubular section 13 with an opening at the first end 11. The tubular section 13 extends a distance toward the second end 12, and has an inner diameter $d_1$ and a length adapted to accommodate a portion of the core member 2 as described below. An end surface 13a of the tubular section provides a stop for the insertion of the core member 2. The second end 12 of the anchor member 1 is formed as a tip portion. At least a portion of an outer surface of the anchor member 1 is provided with a bone engagement structure 14 that is configured to engage a bone or a vertebra when the anchor member 1 is used. In the embodiment shown, the bone engagement structure 14 includes a bone thread that extends over substantially the length of the anchor member 1, but it may also only extend over a smaller portion of the outer surface of the anchor member 1.

The anchor member 1 may be made of a material that has a higher modulus of elasticity than that of the material of the core member 2, meaning, the anchor member 1 is made of a stiffer material than the core member 2. In some embodiments, the anchor member 1 is made of titanium or stainless steel. The anchor member 1 can also be made of a biocompatible polymer material, where the dimensions, such as the length and wall thickness of the anchor member are such that the anchor member does not exhibit a flexible behavior when inserted into a bone.

As shown in FIGS. 4 and 5, the core member 2 is a longitudinal member comprising a first end 21, an opposite second end 22, and a substantially rod-shaped central portion 23. The central portion 23 has a circular cross-section with an outer diameter $d_2$ that is smaller than the inner diameter $d_1$ of the tubular section 13 of the anchor member 1. Adjacent to the first end 21, there is a first connection portion 21a, and adjacent to the second end 22, there is a second connection portion 22a. As can be seen in particular in FIG. 5, the first and second connection portions 21a, 22a, respectively, have an outer contour of a square with rounded edges. A distance $d_3$ from one flat side to an opposite flat side of the square contour is slightly greater than the outer diameter $d_2$ of the central portion 23 of the core member 2 such that the second connection portion 22a may be connected in a press-fit manner in the tubular section 13 of the anchor member 1, as explained below. The second connection portion 22a has a length in an axial direction adapted to provide sufficient fixation within the tubular section 13. The first connection portion 21a at the first end 21 connects with the head 3, and has a shape similar to that of the second connection portion 22a. Between the central portion 23 and each of the first and second connection portions 21a, 22a, respectively, there is a transition portion each of 21b, 22b, respectively, with increasing outer diameter towards its respective connection portion 21a, 22a. The total length of the core member 2 is such that when the core member 2 is inserted into the anchor member 1, and the second end 22 of the core member 2 abuts against the end surface 13a of the tubular section 13 of the anchor member 1, at least the first connection portion 21a and the first transition portion 21b of the core member 2 project out of the open first end 11 of the anchor member 1.

The core member 2 is made of a material that is based on a nickel-titanium based shape memory alloy, preferably from Nitinol. The material exhibits superelasticity. Superelasticity is present in the austenitic metallurgical state. In particular, superelasticity is present in a temperature range slightly above the stress-free martensite to austenite transition temperature, which should be the temperature range of use and includes body temperature. In one emodiment, the core member 2 is made of a nickel-titanium based shape memory alloy of the ELI (extra low interstitial) type, in particular Nitinol of the ELI type. Such a material is of high purity, and in particular, comprises less oxygen compared to other Nitinol alloys that are not of the ELI type. For example, the oxygen content may be less than 0.025 wt %, preferably equal to or less than 0.010 wt %, and more preferably equal to or less than 0.005 wt %. The material has a fatigue strength limit that can be up to two times higher than non-ELI type shape memory alloys.

The head 3 will be described with reference to FIGS. 6 and 7. The head 3 comprises a first end 31, an opposite second end 32, and a spherical-segment shaped portion 33 adjacent to the first end 31. An engagement portion 34 for engagement with a driver is at a free end surface of the first end 31. Adjacent to the spherical-segment shaped portion 33, there is a cylindrical neck portion 35 with a cylindrical recess 36 for accommodating the first connection portion 21a of the core member 2. The length and an inner diameter of the recess 36 is such that the first connection portion 21a can be accommodated therein with a press-fit connection.

FIGS. 8a to 9b illustrate steps of manufacturing the dynamic bone anchor according to the first embodiment. First, the core member 2 may be pre-assembled with the head 3 by connecting the first connection portion 21a to the cylindrical recess 36 of the head 3 in a press-fit manner. The second connection portion 22a may be previously or already shaped in its final shape, as shown in FIGS. 4 and 5. Then, at least the second connection portion 22a of the core member may be cooled down below a martensite finish temperature $M_f$, resulting in a phase transition of the material from austenite into martensite.

As shown in FIG. 8a, a modular system may be provided comprising at least two anchor members 1, 1', that differ, for example, in their shaft lengths. The core member 2 may be selectively introduced into the tubular section 13 of one of the at least two anchor members 1, 1'.

Referring to FIG. 9a, the pre-assembled core member 2 with the head 3 is introduced into the tubular section 13 of one of the anchor members 1, 1', until the second end 22 of the core member 2 abuts against the end surface 13a of the tubular section 13. Thereby, the second connection portion 22a of the core member 2 is deformed such that, for example, the flat sides are impressed so that they have a smaller distance from each other than in the original shape, as depicted in FIG. 8b. Accordingly, the second connection portion 22a of the core member 2 can be introduced into the tubular section 13 of the anchor member 1. Due to the ability of the martensite phase to deform, the insertion can be achieved with low force and little abrasion.

In a next step, heating the second connection portion 22a above the austenite finish temperature $A_f$ effects a phase transition from martensite to austenite and a change of shape of the second connection portion 22a back to its original shape with the rounded square contour as shown in FIG. 9b resulting from the shape memory of the material. Hence, the manufacturing process uses the shape memory behavior of the core member 2. By means of this procedure and the square shape of the second connection portion 22a, a particularly strong press-fit connection can be achieved through a distortion-fit connection using the shape memory effect, which is stronger than a press-fit connection based on conventional machining techniques.

It should be noted that the connection between the core member 2 and the head 3 can also be made in the same manner described above.

Figure 10:
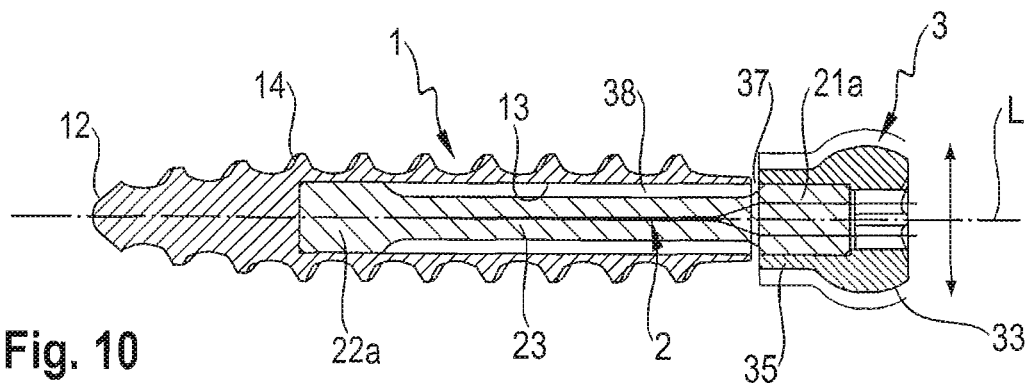
FIG. 10: shows a cross-sectional view of the dynamic bone anchor according to the first embodiment illustrating a translational movement of the head relative to the anchor member.

Referring to FIG. 10, in the assembled state, there is a gap 37 between the second end 32 of the head 3 and the first end 11 of the anchor member 1. Also, there is a gap 38 between the central portion 23 of the core member 2 and a wall of the tubular section 13. These gaps 37, 38 allow the head 3 to perform translational movement with respect to the anchor member 1 in a direction substantially perpendicular to the anchor axis L. The extent of deflection from the central axis L of the bone anchor depends on the elasticity of the material of the core member 2 and the size of the gaps 37, 38, which depend on the thickness and length of the core member 2. A translation movement may occur when the deflection of the core member 2 is mostly in the region of the first connection portion 21a.

Figure 11:
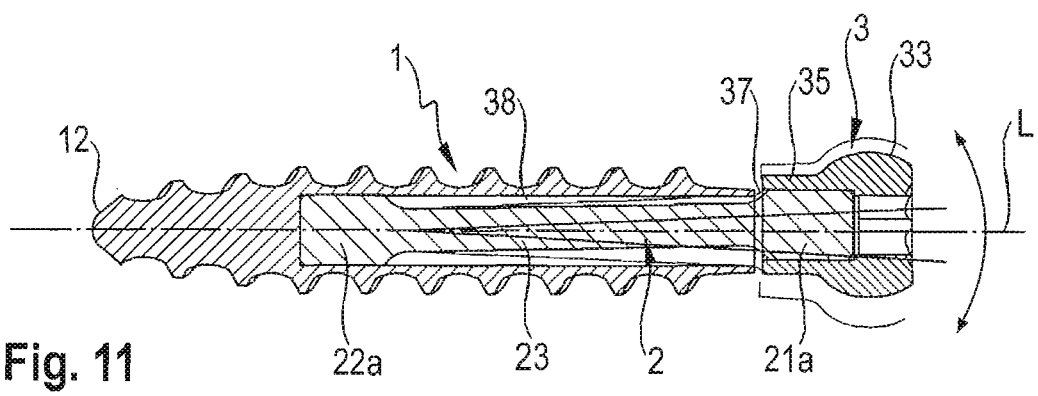
FIG. 11: shows a cross-sectional view of the dynamic bone anchor according to the first embodiment illustrating a rotational movement of the head relative to the anchor member.

Referring to FIG. 11, also a rotational movement of the center point of the head 3 around the anchor axis L is possible. For the rotational movement, the deflection of the core member takes place almost over the whole length of the central portion 23 and the first connection portion 21a. Due to the superelasticity of the material of the core member 2 a deflection of the core member 2 out of the anchor axis is possible with a core member that is shorter compared to a core member made of another metallic material.

Figure 12:
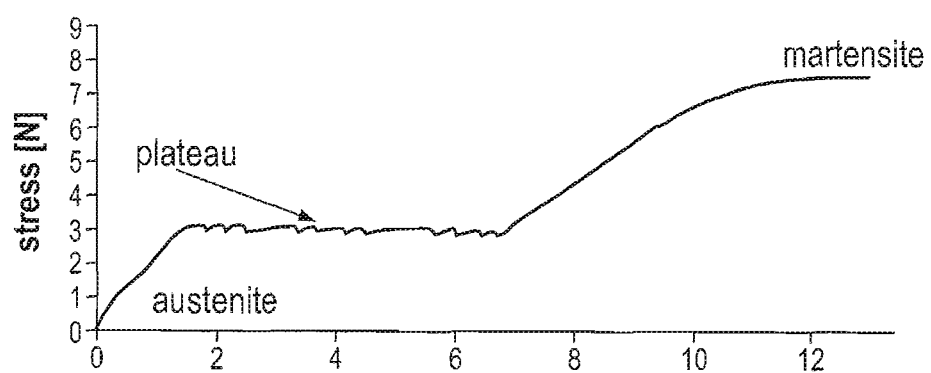
FIG. 12: shows an exemplary stress-strain diagram of the bone anchor according to one embodiment.

In use, the dynamic bone anchor is inserted into a bone part or a vertebra. Because the core member 2 is in the austenitic metallurgical state and in the conditions of use, the core member 2 has superelastic characteristics. In the stress-strain diagram of the bone anchor shown in FIG. 12, a stress-strain plateau is shown. Because of the plateau, the force acting onto the head 3 during screwing-in of the bone anchor remains constant over a certain range such that an overloading of the anchor head 3 may not occur.

In the anchored state, the head 3 is capable of performing a limited motion. The motion is constrained by the abutment of the core member 2 against the inner surface of the tubular section 13 of the anchor member 1.

Figure 13:
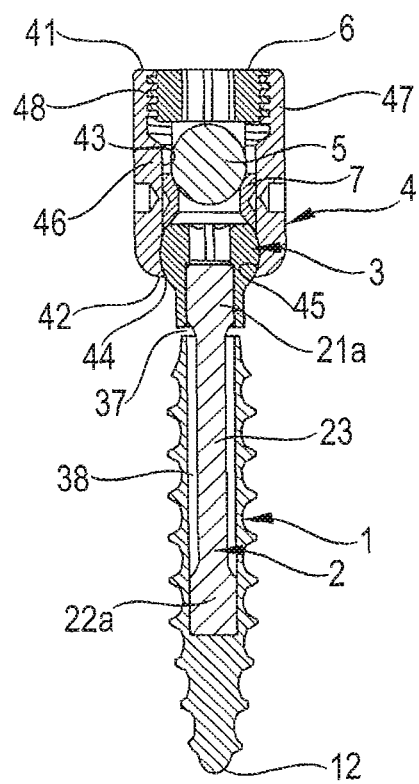
FIG. 13: shows a cross-sectional view of a polyaxial pedicle screw using the dynamic bone anchor according to the first embodiment as an anchoring element.

A first application of the bone anchor together with a stabilization device is shown in FIG. 13. The bone anchor according to the first embodiment is coupled to a receiving part 4 to form a polyaxial bone anchor. The receiving part 4 is substantially cylindrical and comprises a top end 41, a bottom end 42, and a coaxial bore 43 extending from the top end 41 to a distance from the bottom end 42. The bore 43 narrows towards the bottom end 42 and has an opening 44 near the bottom end 42. Near the opening 44, a seat 45 is provided for pivotably receiving the head 3. A U-shaped recess extends from the top end 41 to a distance from the top end 41 for receiving a stabilization rod 5. The U-shaped recess creates two free legs 46, 47, which have an internal thread 48 for cooperating with a locking member 6, such as a set screw. Furthermore, a pressure member 7 is provided that exerts pressure onto the head 3 such that the head 3 can be locked in a certain angular position by tightening the locking member 6. The bone anchor may be used with other designs of receiving parts and polyaxial bone screws. Also, the head 3 of the core member 2 may be designed such that it comprises a section for receiving a rod and for receiving a locking member to fix the rod, as known from other monoaxial bone screws. In use, at least two polyaxial bone anchors may be used and connected via the rod 5. Once the anchor members 1, 1' are inserted into the bone parts or adjacent vertebrae, the heads 3, 3' can perform a limited motion with respect to the anchor members 1, 1', respectively. Once each head 3, 3' is locked in its respective receiving part 4, the bone anchor provides for a dynamic stabilization that allows small movements of the bone parts with respect to each other, or small movements of a motion segment of the spinal column.

Figure 14:
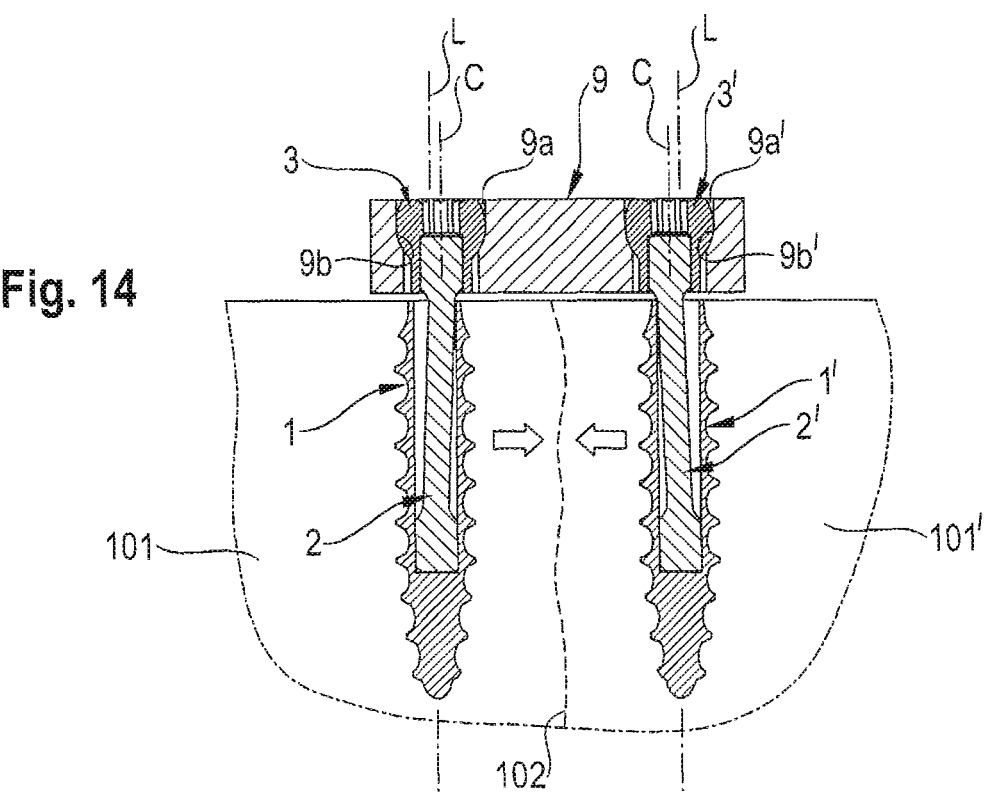
FIG. 14: shows a cross-sectional view of the dynamic bone anchor according to the first embodiment used with a bone plate to provide dynamic fixation to bone parts.

A second example of application of the bone anchor according to another embodiment is shown in FIG. 14. In this embodiment, the dynamic bone anchors according to the first embodiment are used together with a bone plate 9 comprising holes 9*a*, 9*a'* with seat portions 9*b*, 9*b'* for receiving the heads 3, 3' of two bone anchors 1, 1', respectively. The two bone anchors 1, 1' are inserted in adjacent bone parts 101, 101' and the bone plate 9 bridges at least a portion of a fracture site 102. In a specific application, a distance between the central anchor axes C of the two holes 9*a*, 9*a'* that accommodate the heads 3, 3' of the bone anchors, respectively, is slightly smaller than the distance between the longitudinal axes L of the anchor members 1, 1'. Because the core members 2, 2' with the heads 3, 3' can perform a limited motion in a direction transverse to the longitudinal axis L, the bone parts 101, 101' can be drawn together at the fracture site 102 as shown by the arrows in FIG. 14.

Referring to FIGS. 15 to 17, a second embodiment of the dynamic bone anchor is described. The dynamic bone anchor according to the second embodiment differs from the dynamic bone anchor according to the first embodiment in that the anchor member 1" is formed completely as a tubular member 13". That means, the anchor member 1" is open at the first end 11 and at the second end 12. The core member 2" includes a tip 24 between the second connection portion 22*a* and the second end 22. The second connection portion 22*a* is configured to be fixed in the previously described manner via a distortion-fit connection using the shape memory effect to the portion adjacent to the second end 12 of the anchor member 1". The tip 24 of the core member 2" projects out of the open second end 12 of the anchor 1". The tip 24 may have a smooth surface or may have further features, such as a self tapping structure, barbs, or a roughened surface, etc. All other parts of the dynamic bone anchor according to the second embodiment are similar to the first embodiment and the description thereof is not repeated.

Figure 18:
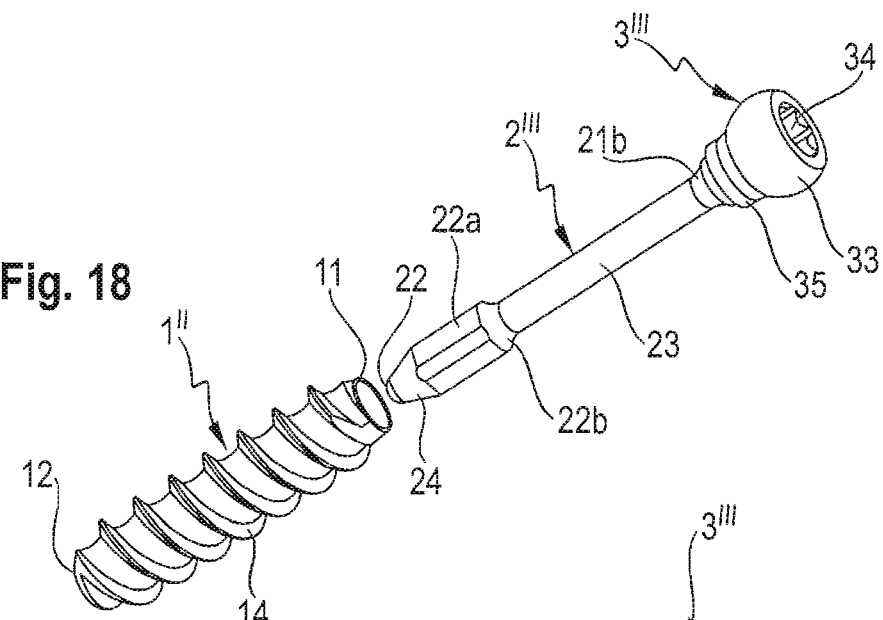
FIG. 18: shows a perspective exploded view of the dynamic bone anchor according to a third embodiment.
Figure 19:
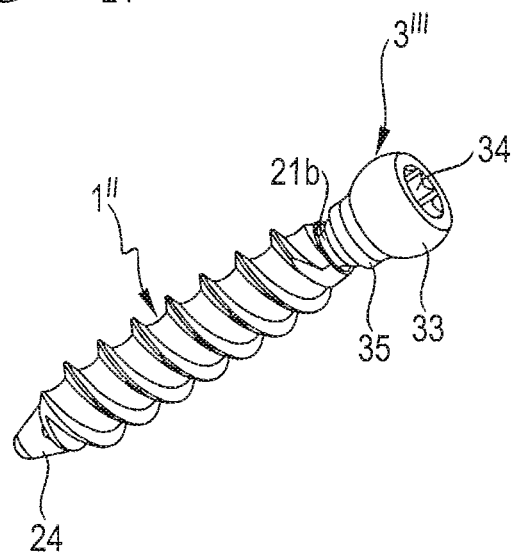
FIG. 19: shows a perspective view of the dynamic bone anchor according to FIG. 18 in an assembled state.
Figure 20:
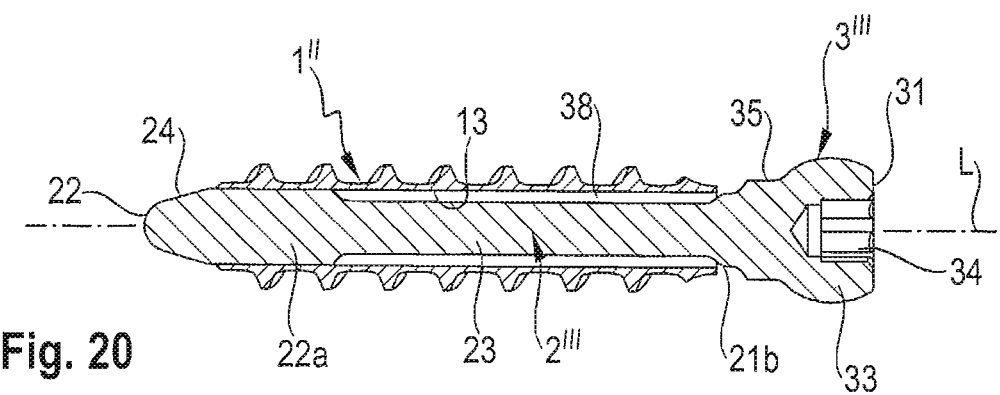
FIG. 20: shows a cross-sectional view of the dynamic bone anchor according to the third embodiment, the cross-section taken in a plane containing the anchor axis.

Referring to FIGS. 18 to 20, a third embodiment of the dynamic bone anchor will be described. The bone anchor according to third embodiment differs from the bone anchor according to the second embodiment in that the core member 2''' comprises a head 3''' similar to the head 3 of the first embodiment at the first end 21, wherein the head 3''' is formed integrally with the central portion 23 of the core member 2'''. Hence, the core member 2''' with head 3''' is a monolithic piece, and the entire dynamic bone anchor comprises only two pieces. The outer contour of the head 3''' is similar to the head 3 according to the first embodiment as previously described.

Further adaptations or modifications of the dynamic bone anchor described in the embodiments can be accomplished by one of ordinary skill in the art without departing from the scope of the invention. For example, the head may have any other shape suitable for connecting it to other stabilization devices such as bone plates, receiving parts for accommodating stabilization rods etc. The head may even be omitted if a free end of the core member is suitable for connection to another device. In such a case, the free end of the core member may comprise an engagement portion for a driver. In both cases, with or without a head or a head portion, the engagement portion of the bone anchor for engagement with a tool is at a movable end of the core member.

Any kind of tip may be provided. The tip shown in the embodiments may even be omitted. For example, the hollow tubular anchor member according to the second and third embodiments, may have prongs at the second end.

The bone engagement structure may be a bone thread of any type suitable for engaging the bone, or may be accomplished by barbs or may even be only a roughened surface.

The embodiments may also be combined among each other, only as an example for such a combination, the anchor member of the first embodiment may include a core member having an integrally formed head, as described in the third embodiment.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:

1. A dynamic bone anchor comprising:
   an anchor member having a first end and a second end, a tubular section between the first end and the second end having an inner surface defining a bore, the inner surface having an inner width, a longitudinal axis extending from the first end to the second end, an outer surface, and a bone engagement structure for engaging a bone on at least a portion of the outer surface; and
   a longitudinal core member having a first portion and a second portion, the second portion configured to be received in the tubular section and to be connected thereto, wherein the second portion has a first outer width that defines a greatest outer width of the second portion, and wherein the second portion is made at least partially of a first material that comprises a shape memory alloy having a temperature sensitive property,
   wherein in a first configuration where the anchor member and core member are separated and the core member is at a first temperature, the first outer width of the second portion of the core member is larger than the inner width of the tubular section of the anchor member and the first outer width is configured to be deformed by the tubular section during introduction of the core member into the tubular section, and
   wherein in a second configuration where the core member is inserted into the anchor member and the core member is at a second temperature greater than the first temperature, the first outer width of the second portion of the core member engages the anchor member with a force greater than when the core member is at the first temperature, to connect the core member to the anchor member.

2. The dynamic bone anchor of claim 1, wherein the first temperature is below a martensite finish temperature $M_f$ of the shape memory alloy and the second temperature is above an austenite finish temperature $A_f$ of the shape memory alloy.

3. The dynamic bone anchor of claim 1, wherein the shape memory alloy is Nitinol.

4. The dynamic bone anchor of claim 1, wherein the anchor member is made of a second material that is different from the first material.

5. The dynamic bone anchor of claim 2, wherein in the second configuration, the core member is fixed to the anchor member by a press-fit connection achieved by a process including manufacturing at least the second portion of the core member with a predefined shape, cooling the second portion below the martensite finish temperature $M_f$, deforming the second portion of the core member by reducing the first outer width during insertion into the anchor member to be less than or equal to the inner width of the tubular section of the anchor member, and heating the second portion after insertion into the anchor member thereby using the shape memory effect.

6. The dynamic bone anchor of claim 1, wherein the first portion of the core member comprises an intermediate portion that has an outer width that is smaller than the inner width of the tubular section.

7. The dynamic bone anchor of claim 1, wherein when the second portion of the core member is fully inserted in the tubular section and is connected to the tubular section, the first portion of the core member is deflectable from the longitudinal axis in a translational movement in a direction transverse to the longitudinal axis and/or in a rotational movement around the longitudinal axis.

8. The dynamic bone anchor of claim 7, wherein the first portion of the core member projects out of the tubular section.

9. The dynamic bone anchor of claim 8, wherein a free end of the first portion of the core member is connected to an anchor head having a width greater than the inner width of the tubular section.

10. The dynamic bone anchor of claim 9, wherein the free end of the first portion of the core member is fixed to the anchor head by a press-fit connection achieved by a process including manufacturing the free end of the first portion of the core member with a predefined shape, cooling it below the martensite finish temperature $M_f$, deforming it during insertion into the anchor head, and heating it after insertion into the anchor head thereby using the shape memory effect.

11. The dynamic bone anchor of claim 8, wherein the free end of the first portion of the core member is shaped as an anchor head having a width greater than the inner width of the tubular section, the anchor head being monolithic with other parts of the first portion of the core member.

12. The dynamic bone anchor of claim 11, wherein when the second portion of the core member is fully inserted in the tubular section and is connected to the tubular section, the anchor head is spaced a distance apart from the tubular section such that it can move with respect to the tubular section.

13. The dynamic bone anchor of claim 1, wherein the anchor member comprises a tip at the second end.

14. The dynamic bone anchor of claim 1, wherein the anchor member is open at the second end and wherein the core member extends through the open second end forming a tip of the bone anchor.

15. A dynamic bone anchor comprising:
an anchor member having a first end and a second end, a tubular section between the first end and the second end having an inner surface defining a bore, the inner surface having an inner width, a longitudinal axis extending from the first end to the second end, an outer surface, and a bone engagement structure for engaging a bone on at least a portion of the outer surface; and
a longitudinal core member having a first portion and a second portion, the second portion configured to be received in the tubular section and connected thereto, wherein the second portion has a first outer width that defines a greatest outer width of the second portion, and wherein the second portion is made at least partially of a first material that comprises a shape memory alloy having a temperature sensitive property, wherein the core member is configured to be fixed to the anchor member by a press-fit connection achieved by a process including manufacturing at least the first outer width of the second portion of the core member to have a greater width in an undeformed configuration than the inner width of the anchor member at a first temperature, introducing the second portion of the core member into the tubular section of the anchor member when the second portion is at the first temperature to deform the first outer width of the second portion, and increasing the temperature of the core member from the first temperature to a second temperature to expand the second portion of the core member towards the undeformed configuration after insertion into the anchor member to connect the core member to the anchor member.

16. The dynamic bone anchor of claim 15, wherein the first temperature is below a martensite finish temperature $M_f$ of the shape memory alloy and the second temperature is above an austenite finish temperature $A_f$ of the shape memory alloy.

17. A dynamic bone anchor comprising:
an anchor member having an open first end and a second end, a tubular section between the first end and the second end, a longitudinal axis extending from the first end to the second end, an outer surface, and a bone engagement structure for engaging a bone on at least a portion of the outer surface, wherein the anchor member is made of a first material; and
a longitudinal core member having a first portion and a second portion, the second portion comprising a second end of the core member and configured to be inserted into the open first end of the anchor member to be received in the tubular section and connected thereto, the first portion extending from the second portion to a first end of the core member opposite the second portion, wherein the core member is made of a second material different from the first material, the first material being a stiffer material than the second material;
wherein when the second portion of the core member is fully inserted in the tubular section and is connected thereto, the first portion of the core member is deflectable from the longitudinal axis in a translational movement in a direction transverse to the longitudinal axis or in a rotational movement around the longitudinal axis.

18. The dynamic bone anchor of claim 17, wherein the first end of the core member comprises an anchor head having a width larger than the greatest outer width of the second portion of the core member.

19. The dynamic bone anchor of claim 17, wherein the second material is a shape memory alloy.

* * * * *

UNITED STATES PATENT AND TRADEMARK OFFICE
CERTIFICATE OF CORRECTION

PATENT NO. : 10,751,101 B2
APPLICATION NO. : 16/148723
DATED : August 25, 2020
INVENTOR(S) : Lutz Biedermann et al.

Page 1 of 1

It is certified that error appears in the above-identified patent and that said Letters Patent is hereby corrected as shown below:

In the Claims

Column 10, Line 37 (approx.), Claim 17 delete "connected" and insert -- to be connected --

Signed and Sealed this
Thirteenth Day of July, 2021

Drew Hirshfeld
*Performing the Functions and Duties of the
Under Secretary of Commerce for Intellectual Property and
Director of the United States Patent and Trademark Office*